United States Patent
McKnew

(10) Patent No.: US 11,318,960 B1
(45) Date of Patent: May 3, 2022

(54) REDUCING PATHOGEN TRANSMISSION IN AUTONOMOUS VEHICLE FLEET

(71) Applicant: GM Cruise Holdings LLC, San Francisco, CA (US)

(72) Inventor: Jennifer Devar McKnew, Petaluma, CA (US)

(73) Assignee: GM Cruise Holdings LLC, San Francisco, CA (US)

(*) Notice: Subject to any disclaimer, the term of this patent is extended or adjusted under 35 U.S.C. 154(b) by 117 days.

(21) Appl. No.: 16/875,593

(22) Filed: May 15, 2020

(51) Int. Cl.
| | |
|---|---|
| *B60W 60/00* | (2020.01) |
| *B60W 40/08* | (2012.01) |
| *B60W 50/14* | (2020.01) |
| *G01C 21/34* | (2006.01) |
| *G08G 1/123* | (2006.01) |

(Continued)

(52) U.S. Cl.
CPC ...... *B60W 60/00253* (2020.02); *B60W 40/08* (2013.01); *B60W 50/14* (2013.01); *G01C 21/3415* (2013.01); *G05D 1/0011* (2013.01); *G05D 1/0297* (2013.01); *G08G 1/123* (2013.01); *G08G 1/22* (2013.01); *B60W 2040/0872* (2013.01); *B60W 2420/42* (2013.01); *B60W 2420/52* (2013.01); *B60W 2540/043* (2020.02); *B60W 2540/049* (2020.02);

(Continued)

(58) Field of Classification Search
CPC ........... B60W 60/00253; B60W 40/08; B60W 50/14; B60W 2540/043; B60W 2540/221; B60W 2556/50; B60W 2556/65; B60W 2540/049; B60W 2420/42; B60W 2040/0872; B60W 2420/52; G01C 21/3415; G05D 1/0011; G05D 1/0297; G08G 1/22; G08G 1/123

See application file for complete search history.

(56) References Cited

U.S. PATENT DOCUMENTS

| | | | |
|---|---|---|---|
| 10,131,322 B2* | 11/2018 | Hoyos | H04L 67/12 |
| 10,241,511 B2* | 3/2019 | Regmi | A61B 5/01 |

(Continued)

FOREIGN PATENT DOCUMENTS

| | | | | |
|---|---|---|---|---|
| KR | 101729327 B1 * | 4/2017 | | B60W 60/0016 |
| WO | WO-2020205629 A1 * | 10/2020 | | B60W 40/02 |

OTHER PUBLICATIONS

I. Jeong, S.Jun, D.Lee, and H. Yoon "Development of Bio Signal Measurement System for Vehicles", 2007 International Conference on Convergence Information Technology., IEEE.conference proceedings, pp. 1091-1096. (Year: 2007).*

*Primary Examiner* — Peter D Nolan
*Assistant Examiner* — Tanya C Sienko
(74) *Attorney, Agent, or Firm* — Patent Capital Group

(57) ABSTRACT

An autonomous vehicle (AV) implements a health protocol that may reduce pathogen transmission between users of the AV. The AV is equipped with a thermal sensor that captures a body temperature of a user. The AV compares the user's temperature to a threshold temperature, and if the user's temperature exceeds the threshold temperature, the AV performs checks to ensure that the user's planned trip follows current regulations or recommendations. For example, the AV confirms that the user is traveling between the user's home and a healthcare facility. If the trip is permitted, the AV enables the user to enter the AV. The AV may include a disinfectant system for disinfecting the passenger compartment or surfaces after the user exits the AV.

20 Claims, 5 Drawing Sheets

(51) Int. Cl.
*G08G 1/00* (2006.01)
*G05D 1/00* (2006.01)
*G05D 1/02* (2020.01)

(52) U.S. Cl.
CPC ... *B60W 2540/221* (2020.02); *B60W 2556/50* (2020.02); *B60W 2556/65* (2020.02)

(56) References Cited

U.S. PATENT DOCUMENTS

| | | | |
|---|---|---|---|
| 11,091,166 B1* | 8/2021 | Bielby | G06N 3/084 |
| 2011/0267186 A1 | 11/2011 | Rao et al. | |
| 2017/0330044 A1* | 11/2017 | Telpaz | B60K 35/00 |
| 2019/0258879 A1 | 8/2019 | Vachhani | |
| 2019/0277643 A1* | 9/2019 | Szubbocsev | G01C 21/3453 |
| 2019/0354753 A1* | 11/2019 | Worrall | G06K 9/00087 |
| 2020/0130703 A1* | 4/2020 | Pendelton | G06K 9/00302 |
| 2020/0143940 A1* | 5/2020 | Yasui | B60R 16/02 |
| 2021/0061298 A1* | 3/2021 | Balachandran | B60W 60/0054 |

* cited by examiner

REDUCING PATHOGEN TRANSMISSION IN AUTONOMOUS VEHICLE FLEET

TECHNICAL FIELD OF THE DISCLOSURE

The present disclosure relates generally to autonomous vehicle fleets and, more specifically, to methods and systems for applying health protocols and reducing spread of disease in a ride service provided by an autonomous vehicle fleet.

BACKGROUND

Ridesharing services that use autonomous vehicles (AVs) to provide rides to users may help prevent the spread of disease by not exposing drivers to potentially sick passengers or exposing passengers to potentially sick drivers. However, even without a driver, an AV can pass diseases from sick passengers to healthy passengers. Viruses or bacteria shed by a sick passenger can linger on surfaces of the AV, such as door handles or arm rests, and in the air inside the AV. These lingering pathogens poses a risk to other passengers who ride in the AV, even if the sick and healthy passengers do not ride in the AV at the same time. Other services provided by AV fleets can create similar risks. For example, if a sick person loads an item for delivery into a compartment of the AV, the delivery item, and portions of the AV that the person came into contact with, may be contaminated, which exposes the recipient of the delivery item and other users of the AV to disease.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Overview

Figure 1:
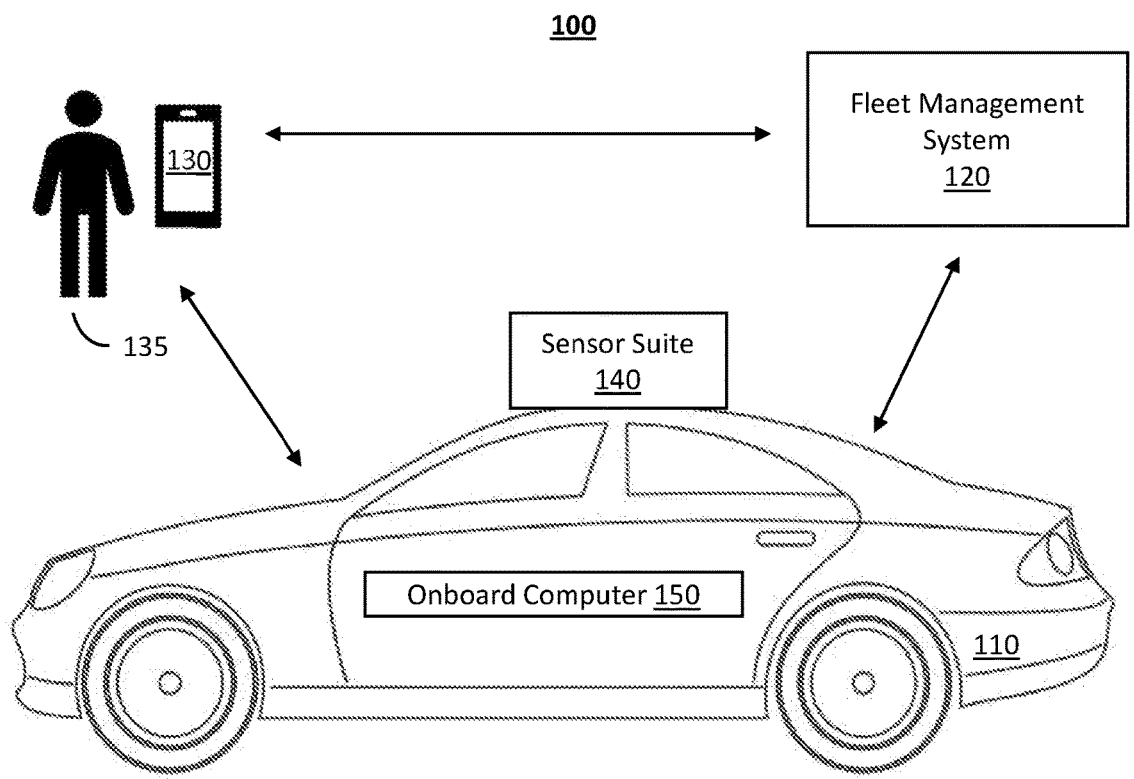
FIG. 1 is a block diagram illustrating a system including an example autonomous vehicle (AV) equipped to reduce spread of disease between users according to some embodiments of the present disclosure.

The systems, methods and devices of this disclosure each have several innovative aspects, no single one of which is solely responsible for all of the desirable attributes disclosed herein. Details of one or more implementations of the subject matter described in this specification are set forth in the description below and the accompanying drawings.

Services that rely on shared vehicles, such as AV-enabled ride or delivery services, can lead to transmission of disease between users who come into contact with the same vehicle. For example, some pathogens, like measles and influenza viruses, can remain airborne for an extended period of time, and a healthy rider who enters an AV after a sick rider has exited the AV may catch the disease from the contaminated air. Other pathogens, like the severe acute respiratory syndrome coronavirus 2 (SARS-CoV-2) virus and noroviruses, can survive on surfaces and be passed to other users who touch the surface; this process is referred to as fomite transmission. The risk to users is especially high during times of high rates of disease, such as during an epidemic or a pandemic.

As described herein, a fleet management system can institute a health protocol or set of health protocols that may prevent a fleet of AVs from transmitting disease between users. The AVs are equipped to assess the health of a user and dynamically adjust one or more user flows based on the determined health status. For example, the AV includes a thermal camera that scans a passenger before the passenger enters the AV. If the passenger has a fever, the AV checks that the passenger is going to a permitted destination, such as a healthcare facility (e.g., a hospital, testing center, or pharmacy) or the passenger's home. During an epidemic or pandemic, people showing symptoms may be banned or discouraged from going to certain kinds of public places (e.g., shops, restaurants, and churches) or from making social visits, and the AV fleet helps enforce these rules or guidelines.

Health protocols implemented by the AV fleet can also reduce exposure in delivery contexts. For example, an AV assesses the health of a user placing an item in an AV and of a user retrieving an item from an AV, e.g., by using a thermal camera to scan a user and determine if the user has a fever. If the AV determines that the user has symptoms, the AV may prevent the user from accessing a delivery compartment of the AV. In some cases, the AV may allow a user to access a delivery compartment, e.g., if a sick user is retrieving medicine that the user has requested for delivery.

The health protocol also ensures that AVs are cleaned regularly and when an AV has been exposed to disease. If an AV is exposed to a symptomatic delivery user, the AV is disinfected before continuing delivery service. If an AV is exposed to a symptomatic passenger, the AV is disinfected before giving a ride to another passenger. For example, an AV may immediately return to a facility for cleaning after dropping off a symptomatic passenger or dropping off a delivery to a symptomatic user. In some embodiments, the AV includes on-board disinfecting equipment, such as a disinfecting mist sprayed in the interior compartment and/or external surfaces (such as door handles) of the AV. In some cases, using the on-board disinfecting system may enable the AV to safely continue service. In addition, the use of on-board disinfecting equipment reduces exposure to facility workers who provide deeper cleaning of AVs before they return to service.

Embodiments of the present disclosure provide a method for operating a ride service that includes detecting, with a thermal sensor mounted on an AV, a body temperature of a user of the AV; comparing the detected body temperature to a threshold temperature; and, in response to determining that the detected body temperature of the user exceeds the threshold temperature, retrieving a destination of the user, determining if the destination of the user is a permitted destination for a high temperature passenger, and in response to determining that the destination is a permitted destination, enabling the user to enter a passenger compartment of the AV.

Embodiments of the present disclosure further provide an AV that includes a thermal sensor, a thermal image processor, a health protocol engine, and a user access engine. The thermal sensor is mounted on an exterior of the AV and is configured to capture a thermal image of a portion of an environment of the AV. The thermal image processor is configured to determine, based on the thermal image, a body temperature of a user of the AV. The health protocol engine is configured to compare the body temperature to a threshold temperature and, in response to determining that the body temperature exceeds the threshold temperature, determine that a destination of the user is a permitted destination for a high temperature passenger. The user access engine is configured to enable the user to enter a passenger compartment of the AV in response to a signal from the health protocol engine indicating that the user is permitted to enter the AV.

Embodiments of the present disclosure further provide a system for managing a fleet of AVs including a user interface server, a vehicle manager, and a health protocol manager. The user interface server is configured to receive a request for a ride from a user, the request comprising an origin location and a destination location. The vehicle manager is configured to instruct a selected AV of the fleet to drive to the origin location. The health protocol manager is configured to instruct the selected AV to determine a body temperature of the user at the origin location prior to enabling the user to access the AV, and, in response to receiving a signal from the selected AV indicating that the body temperature of the user exceeds a threshold temperature, instruct the selected AV to drive to an AV facility for cleaning after the AV reaches the destination location.

Embodiments of the present disclosure further provide an AV including a thermal sensor, a thermal image processor, a health protocol engine, and a user access engine. The thermal sensor is mounted on an exterior of the AV and is configured to capture a thermal image of a portion of an environment of the AV. The thermal image processor is configured to determine, based on the thermal image, a body temperature of a user of the AV. The health protocol engine is configured to compare the body temperature to a threshold temperature and, in response to determining that the body temperature exceeds the threshold temperature, determine that the user is not presently permitted to access the vehicle. The user access engine is configured to selectively enable the user to access at least one compartment of the AV in response to a signal from the health protocol engine indicating that the user is permitted to access the AV.

Embodiments of the present disclosure further provide a method for operating a delivery service that includes detecting, with a thermal sensor mounted on an exterior of an AV, a body temperature of a user of the AV, the user having an item for loading into the AV; comparing the detected body temperature to a threshold temperature; and, in response to determining that the detected body temperature of the user exceeds the threshold temperature, preventing the user from loading the item into the AV, and alerting a recipient of the item that the user was prevented from loading the item into the AV.

Embodiments of the present disclosure further provide a method for operating a delivery service that includes detecting, with a thermal sensor mounted on an exterior of an AV, a body temperature of a user of the AV, where the user is a recipient of an item loaded in a compartment of the AV; comparing the detected body temperature to a threshold temperature; and, in response to determining that the detected body temperature of the user exceeds the threshold temperature, enabling the user to access the compartment of the AV in which the item is loaded, and disinfecting at least a portion of the AV with which the user contacts while accessing of the compartment.

As will be appreciated by one skilled in the art, aspects of the present disclosure, in particular aspects of applying health protocols by AVs, described herein, may be embodied in various manners (e.g., as a method, a system, a computer program product, or a computer-readable storage medium). Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by one or more hardware processing units, e.g. one or more microprocessors, of one or more computers. In various embodiments, different steps and portions of the steps of each of the methods described herein may be performed by different processing units. Furthermore, aspects of the present disclosure may take the form of a computer program product embodied in one or more computer-readable medium(s), preferably non-transitory, having computer-readable program code embodied, e.g., stored, thereon. In various embodiments, such a computer program may, for example, be downloaded (updated) to the existing devices and systems (e.g. to the existing perception system devices and/or their controllers, etc.) or be stored upon manufacturing of these devices and systems.

The following detailed description presents various descriptions of specific certain embodiments. However, the innovations described herein can be embodied in a multitude of different ways, for example, as defined and covered by the claims and/or select examples. In the following description, reference is made to the drawings where like reference numerals can indicate identical or functionally similar elements. It will be understood that elements illustrated in the drawings are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

The following disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

As described herein, one aspect of the present technology is the gathering and use of data available from various sources to improve quality and experience. The present disclosure contemplates that in some instances, this gathered data may include personal information. The present disclosure contemplates that the entities involved with such personal information respect and value privacy policies and practices.

Other features and advantages of the disclosure will be apparent from the following description and the claims.

Example System for Reducing Spread of Disease by AVs

FIG. 1 is a block diagram illustrating a system including an example autonomous vehicle (AV) equipped to reduce spread of disease between users according to some embodiments of the present disclosure. The system 100 includes an AV 110, a fleet management system 120, and a user device 130. AV 110 includes a sensor suite 140 and an onboard computer 150. The fleet management system 120 may manage a fleet of AVs that are similar to AV 110; the other AVs in the fleet may also include a sensor suite and onboard computer. The fleet management system 120 receives service requests for the AVs 110 from user devices 130. For example, a user 135 makes a request for a ride in an app executing on the user device 130, which transmits the request to the fleet management system 120. The fleet management system 120 dispatches the AVs 110 to carry out the service requests. The fleet management system 120 may instruct the AV 110 to carry out a health protocol during the service request in certain situations, such as an epidemic or pandemic. For example, when the AV 110 reaches the user 135, the sensor suite 140 captures data about the user 135, such as the body temperature of the user 135. The onboard computer 150 processes data from the sensor suite 140 and follows a procedure for handling symptomatic users, such as ensuring that symptomatic users are taking only permitted trips and are following other recommendations or regulations while the health protocol is in place.

The AV 110 is preferably a fully autonomous automobile, but may additionally or alternatively be any semi-autonomous or fully autonomous vehicle; e.g., a boat, an unmanned aerial vehicle, a self-driving car, etc. Additionally, or alternatively, the AV 110 may be a vehicle that switches between a semi-autonomous state and a fully autonomous state and thus, the AV may have attributes of both a semi-autonomous vehicle and a fully autonomous vehicle depending on the state of the vehicle.

The AV 110 may include a throttle interface that controls an engine throttle, motor speed (e.g., rotational speed of electric motor), or any other movement-enabling mechanism; a brake interface that controls brakes of the AV (or any other movement-retarding mechanism); and a steering interface that controls steering of the AV (e.g., by changing the angle of wheels of the AV). The AV 110 may additionally or alternatively include interfaces for control of any other vehicle functions, e.g., windshield wipers, headlights, turn indicators, air conditioning, etc.

The AV 110 includes a sensor suite 140, which includes a computer vision ("CV") system, localization sensors, and driving sensors. For example, the sensor suite 140 may include photodetectors, cameras, radar, sonar, lidar, GPS, wheel speed sensors, inertial measurement units (IMUS), accelerometers, microphones, strain gauges, pressure monitors, barometers, thermometers, altimeters, etc. The sensors may be located in various positions in and around the AV 110. For example, the sensor suite 140 includes multiple cameras mounted at different positions on the AV 110. The sensor suite 140 includes one or more thermal sensors, such as a thermographic camera or an infrared thermometer.

An onboard computer 150 is connected to the sensor suite 140 and functions to control the AV 110 and to process sensed data from the sensor suite 140 and/or other sensors in order to determine the state of the AV 110. Based upon the vehicle state and programmed instructions, the onboard computer 150 modifies or controls behavior of the AV 110. In addition, the onboard computer 150 can instruct sensors of the sensor suite 140 to capture particular images and/or other sensor data. For example, the onboard computer 150 instructs a thermographic camera of the sensor suite 140 to capture an image of a passenger before the passenger enters the AV 110 and/or after the passenger has entered the AV 110. The onboard computer 150 determines the passenger's body temperature and, if the body temperature exceeds a threshold temperature, the onboard computer 150 applies one or more rules to ensure safety of the passenger, other passengers, and the general public.

The onboard computer 150 is preferably a general-purpose computer adapted for I/O communication with vehicle control systems and sensor suite 140, but may additionally or alternatively be any suitable computing device. The onboard computer 150 is preferably connected to the Internet via a wireless connection (e.g., via a cellular data connection). Additionally or alternatively, the onboard computer 150 may be coupled to any number of wireless or wired communication systems. The onboard computer 150 is described further in relation to FIG. 4.

The fleet management system 120 manages the fleet of AVs, including AV 110. The fleet management system 120 may manage a service that provides or uses the AVs, e.g., a service for providing rides to users with the AVs, or a service that delivers items, such as prepared foods, groceries, or packages, using the AVs. The fleet management system 120 may select an AV from the fleet of AVs to perform a particular service or other task, and instruct the selected AV to autonomously drive to a particular location (e.g., a delivery address). The fleet management system 120 may select a route for the AV 110 to follow. The fleet management system 120 also manages fleet maintenance tasks, such as charging, servicing, and cleaning of the AV. As shown in FIG. 1, the AV 110 communicates with the fleet management system 120. The AV 110 and fleet management system 120 may connect over a public network, such as the Internet. The fleet management system 120 is described further in relation to FIG. 5.

Example AV Applying a Health Protocol

Figure 2:
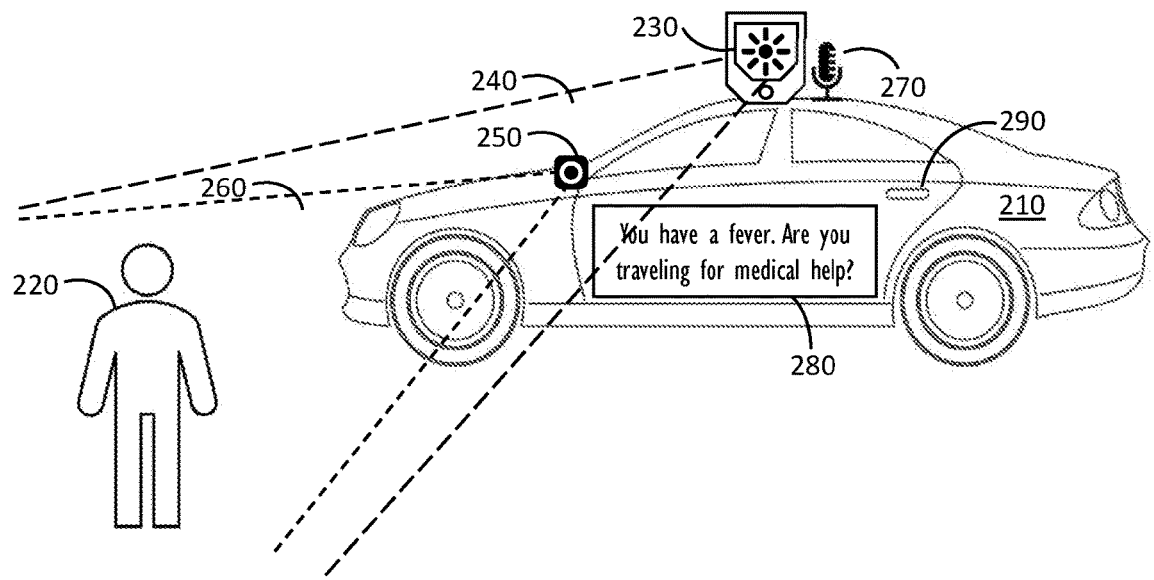
FIG. 2 illustrates an example of an AV applying a health protocol according to some embodiments of the present disclosure.

FIG. 2 illustrates an example of an AV applying a health protocol according to some embodiments of the present disclosure. FIG. 2 shows an AV 210, which is an example of the AV 110 described with respect to FIG. 1. The AV 210 includes a sensor suite similar to sensor suite 140 for capturing data describing the environment of the AV 210. A user 220 is in the environment of the AV 210. In this example, the user 220 is a passenger who requested a ride from a ride service.

The sensor suite includes a thermal sensor 230 mounted on the AV 210 for detecting body temperatures of people in the environment of the AV 210, including the user 220. For example, the thermal sensor 230 is a thermographic camera, also referred to as an infrared camera or thermal imager, that captures images of infrared radiation. The thermal sensor 230 has a field of view 240 that includes the user 220. In some examples, the thermal sensor 230 has a narrower field of view, and the AV 110 and/or a user device (e.g., user device 130) instructs the user 220 to stand at a particular location so that the user's body temperature can be measured. For example, the thermal sensor 230 is an infrared thermometer, and the user device 130 instructs the user to position the user's forehead near the infrared thermometer before proceeding to enter the AV 210. The AV 210 may include multiple thermal sensors 230. For example, the AV 210 has one infrared thermometer on each side of the AV 210, near each door to a passenger compartment of the AV 210, or near each door to each compartment of the AV 210 (e.g., near a door to a delivery compartment). As another example, the AV 210 has enough thermographic cameras to capture a 360° view around the AV 210.

The sensor suite also includes a camera 250 for capturing visual images of the environment of the AV 210. The sensor suite 140 may include multiple cameras 250 to capture different views, e.g., a front-facing camera, a back-facing camera, and side-facing cameras. One or more cameras 250 may be implemented using a high-resolution imager with a fixed mounting and field of view, and one or more cameras 250 may have adjustable field of views and/or adjustable zooms. In the example shown in FIG. 3, the camera 250 has a field of view 260, which includes the user 220.

The AV 210 may use images captured by the camera 250 for various purposes. In one example, an onboard computer of the AV 210 processes the images to determine if the user 220 is wearing recommended or government-mandated personal protective equipment (PPE), such as a facial mask and gloves. As another example, the AV 210 performs image analysis to determine if the user is showing exhibiting physical symptoms (e.g., a rash, blisters, or lesions) associated with a particular disease. For example, the AV 210 may use a machine-learned model trained to identify sick individuals based on photographs to determine a likelihood that the user 220 is sick.

As another example, the AV 210 uses one or more images captured by the camera 250 to identify the user 220, and the AV 210 determines the temperature of the identified user 220 based on the data from the thermal sensor 230. For example, if the user 220 consents, the AV 210 may use facial recognition to identify or verify that the user 220 is associated with the user device 130 that requested the AV 210. Alternatively, the AV 210 may use the camera 250 and/or additional sensors of the sensor suite 140 (e.g., radar sensors, lidar (light detecting and ranging) sensors) to identify which person of multiple people in the environment is the user 220 based on the movements of the people. For example, a perception module connected to the sensor suite receives data from the camera 250 and/or other sensors and tracks the movement in the vicinity of the AV 210. The perception module may identify a person walking towards the AV 210 as the user 220. In some embodiments, the AV 210 identifies the user 220 without using the camera 250; as one example, a Bluetooth sensor connects to a user device (e.g., user device 130) associated with the user 220, and the AV 210 determines that the person holding the user device is the user 220.

The AV 210 also includes user input and output devices for interacting with the user 220. In this example, the AV 210 includes a microphone 270 and a screen 280. The AV 210 may also have a speaker for outputting sound to the user 220. The screen 280 and/or speaker informs the user 220 about current health protocols. For example, the screen 280 instructs the user 220 to stand near the thermal sensor 230 so that the thermal sensor 230 can read the temperature of the user 220. If, as in this example, the thermal sensor 230 detects an elevated body temperature, the screen 280 outputs this information to the user 220. The AV 210 proceeds with a health protocol process for handling passengers with elevated temperatures. As shown in FIG. 2, the screen 280 asks the user 220 to confirm that the user is traveling for medical help. The user 220 may provide a verbal response that is detected by the microphone 270, or a visual response (e.g., a nod) that is detected by the camera 250. The user interface elements may continue a pre-programmed interaction with the user 220, and the AV 210 may determine whether to permit the user 220 to enter the AV 210 based on the user's responses. In other embodiments, a user device (e.g., the user device 130) may conduct the pre-programmed interaction with the user 220, rather than the AV 210.

The AV 210 and/or fleet management system 120 may perform additional checks before permitting the user 220 to ride in the AV 210. For example, the onboard computer of the AV 210 or the fleet management system 120 retrieves the destination location of the user and determine if the user is traveling to a permitted destination, such as a hospital or other medical facility, a pharmacy, or the user's home. The AV 210 or user device 130 may ask for additional information from the user 220 or make additional requests, such as a request for a user to agree to follow any national, state, or local regulations governing the movement and behavior of people during an epidemic, pandemic, or other health event. The AV 210 may confirm that the user 220 has proper PPE for traveling outside the home based on images captured by the camera 250, as described above.

If the AV 210 or fleet management system 120 determines that the user 220 is permitted to ride in the AV 210, the AV 210 enables the user 220 to access the passenger compartment of the AV 210. In the example shown in FIG. 2, the user may use a door handle 290 to open the door to the passenger compartment, and AV 210 unlocks the door handle 290 in response to determining that the user 220 is permitted to ride in the AV 210.

Figure 3:
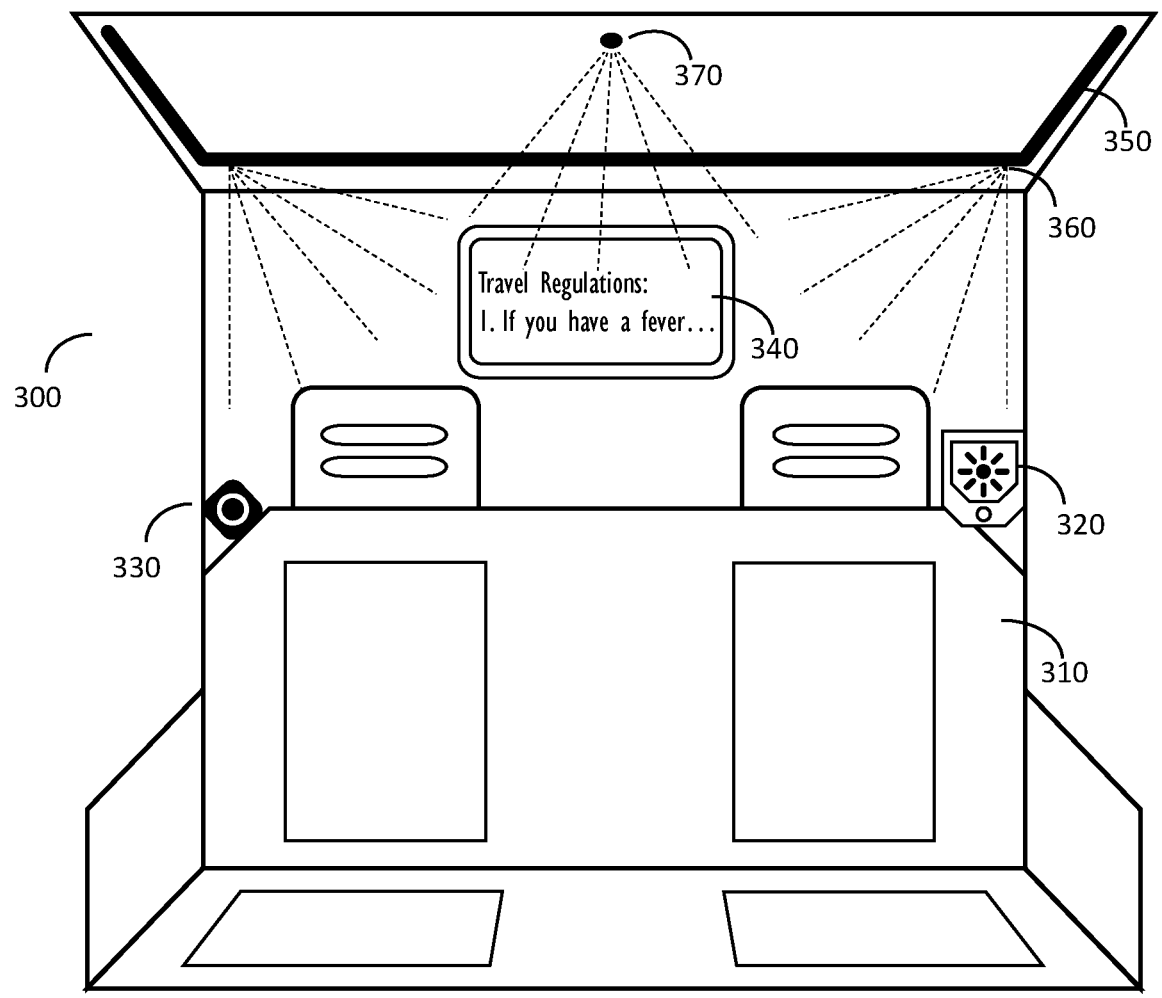
FIG. 3 illustrates an example AV interior configured to apply health protocols according to some embodiments of the present disclosure.

In some embodiments, the interior of the AV 210 is configured to monitor the health status of passengers and communicate with passengers regarding current health protocols. FIG. 3 illustrates an example AV interior configured to apply health protocols according to some embodiments of the present disclosure. In this example, a passenger compartment 300 of the AV 210 has two rows of seats facing each other. The view shown in FIG. 3 is from the viewpoint of one of the rows of seats, looking towards the other row of seats 310. The user 220 may see the view shown in FIG. 3 while seated in the AV 210.

The passenger compartment 300 includes at least one additional thermal sensor 320 and at least one additional camera 330. The thermal sensor 320 is configured to capture a body temperature of a passenger (e.g., user 220) sitting in the passenger compartment 300, and the camera 330 is configured to capture images of the passenger in the passenger compartment 300. The interior thermal sensor 320 and interior camera 330 may be similar to the exterior thermal sensor 230 and exterior camera 250 described with respect to FIG. 2. For example, the interior thermal sensor 320 may be a thermal camera that captures an image including a passenger seated in the passenger compartment 300, or an infrared thermometer directed at head level to capture a passenger's body temperature. In some embodiments, multiple interior thermal sensors are included in the passenger compartment 300, e.g., one directed at each seat or group of seats.

The interior thermal sensor 320 may be used as a backup to the exterior thermal sensor 230, e.g., if the exterior thermal sensor 230 is malfunctioning, or if the temperature reading from the exterior thermal sensor 230 was off. In some cases, the exterior thermal sensor 230 does not detect an elevated temperature in the user 220. After the user 220 enters the AV 210, and before the AV 210 drives away from the location where it picked up the user 220, the interior thermal sensor 320 captures a body temperature of the user 220, and the onboard computer compares the body temperature it to the threshold temperature. If the interior thermal sensor 320 captures an elevated body temperature, the AV 210 may provide health protocol information and/or conduct questioning as described with respect to FIG. 2. The health protocol information and questioning may be provided on an interior screen 340 or the user device 130. During the ride, the interior screen 340 may provide reminders of the current health protocol to the user 220, as shown in FIG. 3. The passenger compartment 300 may further include a speaker, a microphone, and other user interface elements not shown in FIG. 3.

In some embodiments, the passenger compartment 300 includes an interior disinfecting system for disinfecting the vehicle interior. The onboard computer may instruct the interior disinfecting system to apply a disinfectant after a symptomatic passenger exits the AV 210, or after any passenger exits the AV 210. The example interior disinfecting system shown in FIG. 3 includes tubing 350 around the ceiling of the passenger compartment 300. The tubing 350 includes multiple nozzles 360 through which a disinfectant, such as isopropyl alcohol, chlorine, or hydrogen peroxide, is sprayed. The disinfectant kills bacteria and viruses in the air through which the disinfectant travels and on the surfaces on which the disinfectant lands, such as the seats, headrests, and door handles. The disinfectant is sprayed as a fine mist that does not overly saturate or cause damage materials, electronics, or other components within the vehicle interior, including the interior thermal sensor 320, interior camera 330, and interior screen 340. The type of disinfectant may be selected based on the materials and other components within AV; for example, an alcohol-based disinfectant may be selected rather than a bleach-based disinfectant to avoid staining. While two nozzles 360 in the tubing 350 are shown in FIG. 3, fewer or additional nozzles may be included. An additional disinfectant nozzle 370 is positioned in the center of the ceiling of the passenger compartment 300. Alternative arrangements for applying a disinfectant to an AV 110 may be used. For example, the disinfecting system may have disinfectant nozzles arranged to apply disinfectant to parts of the passenger compartment 300 that are frequently touched, such as door handles, the interior screen 340, and phone chargers. In some embodiments, the disinfecting system may include exterior nozzles directed at exterior portions of the AV 210, such as door handles.

Additional or alternative types of disinfecting systems may be included on-board the AV 210 and used for disinfecting the interior and/or exterior of the AV 210. For example, a disinfecting system may include one or more ultraviolet (UV) lamps (e.g., mercury-based lamps, UV light emitting diodes (LEDs), or xenon lamps) that generate UV light for sterilizing surfaces at which the UV light is directed. As another example, the heating, ventilation, and air cooling (HVAC) system raises or lowers the temperature of the passenger compartment to a temperature and for a duration that kills or inactivates one or more types of pathogens.

In some embodiments, the interior and/or exterior cameras 330 and 250 and/or other sensors (e.g., lidar sensors or radar sensors) detect movements of the user and store data describing areas of the AV 210 that the user came into contact with. The AV 210 may selectively disinfect such areas, e.g., by instructing a subset of the nozzles 360 and 370 to distribute the disinfectant. Further, the AV 210 may provide this information to a person cleaning the AV 210 (e.g., via the fleet management system 120) so the person cleaning the AV 210 can focus cleaning efforts on those areas.

Example Onboard Computer

Figure 4:
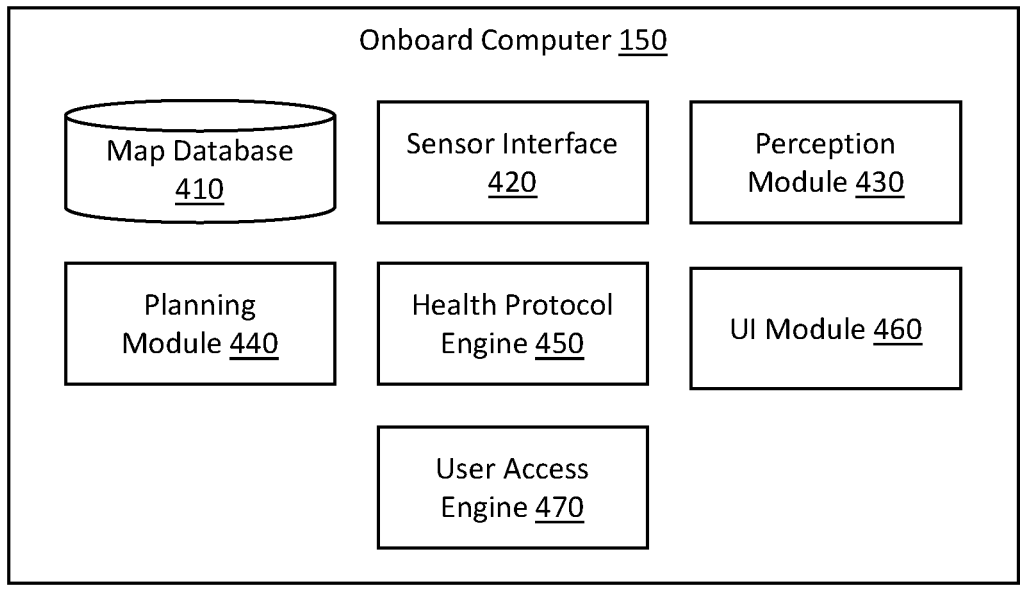
FIG. 4 is a block diagram illustrating an onboard computer according to some embodiments of the present disclosure.

FIG. 4 is a block diagram illustrating the onboard computer 150 according to some embodiments of the present disclosure. The onboard computer 150 includes a map database 410, a sensor interface 420, a perception module 430, a planning module 440, a health protocol engine 450, a user interface (UI) module 460, and a user access engine 470. In alternative configurations, fewer, different and/or additional components may be included in the onboard computer 150. For example, components and modules for controlling movements of the AV 110 and other vehicle functions, and components and modules for communicating with other systems, such as the fleet management system 120, are not shown in FIG. 4. Further, functionality attributed to one component of the onboard computer 150 may be accomplished by a different component included in the onboard computer 150 or a different system from those illustrated.

The map database 410 stores a detailed map that includes a current environment of the AV 110. The map database 410 includes data describing roadways (e.g., locations of roadways, connections between roadways, roadway names, speed limits, traffic flow regulations, toll information, etc.) and data describing buildings (e.g., locations of buildings, building geometry, building types). The map database 410 may further include data describing other features, such as bike lanes, sidewalks, crosswalks, traffic lights, parking lots, etc.

The sensor interface 420 interfaces with the sensors in the sensor suite 140. The sensor interface 420 may request data from the sensor suite 140, e.g., by requesting that a sensor capture data in a particular direction or at a particular time. For example, in response to the perception module 430 determining that the user 220 is in the environment of the AV 110 (e.g., based on images from the camera 250, as described with respect to FIG. 2), the sensor interface 420 instructs the exterior thermal sensor 230 to capture a thermal image or temperature reading of the user 220. As another example, in response to the perception module 430 determining that the user 220 has entered the passenger compartment 300, the sensor interface 420 instructs the interior thermal sensor 320 to capture a thermal image or temperature reading of the user 220. The sensor interface 420 is configured to receive data captured by sensors of the sensor suite 140, including data describing a temperature of the user 220. The sensor interface 420 may have subcomponents for interfacing with individual sensors or groups of sensors of the sensor suite 140, such as a thermal sensor interface, a camera interface, a lidar interface, a radar interface, a microphone interface, etc.

The perception module 430 identifies objects in the environment of the AV 110. The sensor suite 140 produces a data set that is processed by the perception module 430 to detect other cars, pedestrians, trees, bicycles, and objects traveling on or near a road on which the AV 110 is traveling or stopped, and indications surrounding the AV 110 (such as construction signs, traffic cones, traffic lights, stop indicators, and other street signs). For example, the data set from the sensor suite 140 may include images obtained by cameras, point clouds obtained by lidar (light detecting and ranging) sensors, and data collected by radar sensors. The perception module 430 may include one or more classifiers trained using machine learning to identify particular objects. For example, a multi-class classifier may be used to classify each object in the environment of the AV 110 as one of a set of potential objects, e.g., a vehicle, a pedestrian, or a cyclist. As another example, a human classifier recognizes humans in the environment of the AV 110, a vehicle classifier recognizes vehicles in the environment of the AV 110, etc.

In some embodiments, the perception module 430 includes a thermal image processor for processing a thermal image captured by a thermal sensor, e.g., the exterior thermal sensor 230 or interior thermal sensor 320. The thermal image processor determines a body temperature of a passenger of the AV 110 based on the thermal image, e.g., the user 220 standing near the AV 210, or a passenger inside the passenger compartment 300. For example, the thermal image processor identifies a portion of the image, such as a portion of the passenger's face, that accurately represents the passenger's internal body temperature.

The planning module 440 plans maneuvers for the AV 110 based on map data retrieved from the map database 410, data received from the perception module 430, and navigation information, e.g., a route instructed by the fleet management system 120. In some embodiments, the planning module 440 receives map data from the map database 410 describing known, relatively fixed features and objects in the environment of the AV 110. For example, the map data includes data describing roads as well as buildings, bus stations, trees, fences, sidewalks, etc. The planning module 440 receives data from the perception module 430 describing at least some of the features described by the map data in the environment of the AV 110. The planning module 440 determines a pathway for the AV 110 to follow. The pathway includes locations for the AV 110 to maneuver to, and timing and/or speed of the AV 110 in maneuvering to the locations. In some embodiments, the planning module 440 adjusts a pathway based on whether the AV 110 is carrying a symptomatic passenger. For example, the planning module 440 may plan a smoother ride with a lower speed, smoother accelerations and/or decelerations, and/or slower turns in response to a signal from the health protocol engine 450 that a sick passenger is riding in the AV 110. An AV controller (not shown in FIG. 4) instructs the movement-related subsystems of the AV 110 to maneuver according to the pathway determined by the planning module 440.

The health protocol engine 450 implements a health protocol administered by the AV 110. The health protocol engine 450 may select a process for handling a passenger based on data about the passenger gathered by the AV 110 and/or fleet management system 120. For example, the health protocol engine 450 may implement a process to detect symptomatic users, adjust a service provided to a user based on whether the user is symptomatic or not, and sanitize the AV 110 after coming into contact with a symptomatic user. Additionally, or alternatively, the health protocol engine 450 may select a process for interacting with other users of the AV 110, such as users depositing delivery items into the AV 110, and users picking up delivery items from the AV 110.

The health protocol engine 450 may be activated by the fleet management system 120, e.g., during a period of increased disease spread, such as a pandemic or epidemic. The health protocol engine 450 may implement regulations by a local, state, or federal government. Additionally, or alternatively, the health protocol engine 450 may implement recommendations by a government body, task force, healthcare professionals, or other experts. In some embodiments, the health protocol engine 450 is active during periods without increased disease spread. For example, the health protocol engine 450 routinely checks users' temperatures and instructs the AV 110 to return to a facility for cleaning after providing a ride to a symptomatic user.

The health protocol engine 450 receives the body temperature of a user of the AV 110 (e.g., the passenger 220, or a delivery user) from the exterior thermal sensor 230 or the perception module 430. The health protocol engine 450 compares the detected body temperature to a threshold temperature. The threshold temperature may be set in the health protocol as a temperature indicating that the user may be sick. For example, the threshold temperature may be one of 99.5° F., 100° F., 100.4° F., 101° F., etc. The health protocol engine 450 may use alternative or additional information to detect whether the user is symptomatic. For example, the health protocol engine 450 analyzes images of the user captured by the camera 250 to determine if the user appears sick, as described with respect to FIG. 2. As another example, the AV 110 includes additional diagnostic equipment, such as a pulse oximeter, a heart rate monitor, or a blood pressure monitor, and the AV 110 or the user device 130 instructs the user to use the diagnostic equipment. The sensor interface 420 provides data from the diagnostic equipment, and the health protocol engine 450 processes the data to determine whether the user is displaying symptoms.

The health protocol engine 450 selects a user flow based on whether the user is symptomatic, e.g., if the detected body temperature exceeds the threshold temperature. If the health protocol engine 450 does not determine that the user is symptomatic (e.g., the health protocol engine 450 does not detect an elevated body temperature), the health protocol engine 450 allows the user to access the vehicle normally, e.g., by instructing the user access engine 470 to enable a passenger to enter the passenger compartment by unlocking a door to the passenger compartment, or to enable a delivery user to access a delivery compartment by unlocking a door to the delivery compartment. If the health protocol engine 450 detects that the user is symptomatic (e.g., the health protocol engine 450 detects an elevated body temperature), the health protocol engine 450 prevents the user from accessing the AV 110, or permits access only under certain conditions. In addition, the health protocol engine 450 alerts the fleet management system 120 of the sick passenger. The health protocol engine 450 or fleet management system 120 instructs the planning module 440 to navigate to a cleaning facility for disinfecting the AV 110 after the passenger has been dropped off. In addition, or alternatively, the health protocol engine 450 instructs an on-board disinfecting system, such as the system shown in FIG. 3, to apply a disinfectant to the passenger compartment 300 or other areas of the AV 110. In some cases, if the life span of the pathogen in the air or on surfaces is short (e.g., less than an hour, or less than four hours), the AV 110 is taken out of service for at least as long as life span of the pathogen and then resumes service, with or without additional disinfecting measures.

In some embodiments, the health protocol engine 450 permits a symptomatic user to enter the passenger compartment 300 in response to determining that the user is traveling a permitted route, e.g., from home to a healthcare facility, or home from a healthcare facility. In one embodiment, the health protocol engine 450 retrieves a destination of the user and determines if the destination of the user is a permitted destination for a symptomatic passenger. The health protocol engine 450 may also retrieve a pickup location of the user (e.g., the current location of the AV 110, or a pickup location input by the user when requesting a ride) and determine if the pickup location is a permitted pickup location for a symptomatic passenger. A list of permitted destinations, or types of permitted destinations, may be established by a government or health authority. For example, permitted destinations may include users' homes and healthcare facilities, including hospitals, medical offices, mobile healthcare centers, medical testing centers, and pharmacies. A list of permitted pickup locations may include the same set of locations. For example, a user may be permitted to travel from the user's home to a healthcare facility, from a healthcare facility back to the user's home, or between two healthcare facilities.

To determine if a destination or pickup location is a healthcare facility, the health protocol engine 450 may access a list of all permitted healthcare destination addresses and compare the destination address or pickup address to the list. Alternatively, the health protocol engine 450 may retrieve a building type associated with the destination or pickup location of the user from the map database 410 and determine based on the building type if the location is associated with a healthcare service. To determine if a destination or pickup location is a user's home, the health protocol engine 450 may retrieve a home address for the user, compare the retrieved home address to the destination or pickup location, and determine if the destination or pickup location matches the retrieved home address. Determining the user's home address is described further with respect to FIG. 5.

In other examples, permitted destinations may include stores for groceries and other household supplies, restaurants offering drive-through or pickup service, childcare facilities, residential buildings, and/or other types of destinations. In some examples, the health protocol engine 450 has one list of permitted destinations for symptomatic passengers, and another, longer list of permitted destinations for non-symptomatic passengers.

In some embodiments, if the health protocol engine 450 determines that the user is exhibiting symptoms but has not entered a permitted destination, the health protocol engine 450 determines an alternate destination and provides it to the user in a user interface, such as a user interface of the user device 130, one or more user interface devices of the AV 110 (e.g., the exterior screen 280, the interior screen 340, or exterior or interior speakers). For example, the health protocol engine 450 identifies a testing site or health services site with capacity to see the user and provide medical assistance. The user may select the alternate destination and make a modified ride request via the user interface. In response to receiving the alternate ride request, the health protocol engine 450 instructs the user access engine 470 to enable the user to enter the passenger compartment.

In some embodiments, the health protocol engine 450 performs continuous monitoring of a sick patient. For example, if the health protocol engine 450 receives continuous or periodic monitoring signals from the thermal sensor 320 and any additional diagnostic equipment included in the AV 210, such as a pulse oximeter, heart rate monitor, a blood pressure monitor. In response to a change in one or more of the monitoring signals, the health protocol engine 450 may change the destination of the AV 110. For example, if a measured blood pressure goes above an upper threshold or below a lower threshold, or if a temperature exceeds a second, higher threshold temperature (i.e., a higher temperature above the threshold temperature indicating that the user is symptomatic), the health protocol engine 450 determines that the passenger may be having a medical emergency and reroutes the AV 110 to an emergency room or urgent care center.

In some embodiments, the health protocol engine 450 enforces a rule that a symptomatic passenger cannot ride together with a second passenger except in certain circumstances. In some embodiments, this regulation applies to all passengers, including those that do not show symptoms. Exceptions may include if the second passenger lives in the same household as the symptomatic passenger, or if the symptomatic passenger is authorized to have a companion or assistant (e.g., if the symptomatic passenger is a child, elderly, or disabled). As an example, the perception module 430 determines that a symptomatic passenger is accompanied by a second person, e.g., based on data from the camera 250, a lidar sensor, or a radar sensor, or a combination of sensor data. The health protocol engine 450 then verifies the second passenger as a permitted companion based on an identity of the second passenger and a relationship between the symptomatic passenger and the second passenger, and enables the second passenger to enter the AV 110 (e.g., enables both the symptomatic passenger and the second passenger to enter) in response to the verification. To verify the second passenger as a permitted companion, the health protocol engine 450 may retrieve previously provided companion information provided by the symptomatic passenger to the fleet management system 120 via the user device 130. As another example, the health protocol engine 450 receives data about the second passenger, e.g., an image of a driver's license shown to the camera 250, and the health protocol engine 450 compares the home address on the driver's license to a home address of the symptomatic passenger to determine if they live at the same address.

The health protocol engine 450 may enforce additional or alternative regulations based on current recommendations and guidelines, and the type of disease being prevented. For example, the health protocol engine 450 may enforce a regulation that people in public wear PPE; in this example, the health protocol engine 450 processes images received from the camera 250 or 330 to determine if the user is wearing recommended or government-mandated personal protective equipment (PPE), such as a facial mask and gloves. If a user is not wearing the recommended PPE, the health protocol engine 450 may instruct the UI module 460 to inform the user, and instruct the user access engine 470 to not enable the user to enter the AV 110. If a delivery user is not wearing the recommended PPE, the health protocol engine 450 may instruct the user access engine 470 to not enable the delivery user to access a delivery compartment.

The UI module 460 provides information to a user regarding the current health protocol through a user interface, e.g., the exterior screen 280, the interior screen 340, exterior or interior speakers, or a combination of user interface devices. For example, the UI module 460 notifies the user that the user's detected body temperature exceeds the threshold temperature. The UI module 460 may alert a user to regulations governing the movement of people with symptoms of an illness (e.g., elevated body temperature), including regulations implemented by the AV 110. For example, the UI module 460 alerts the user that people with symptoms may only leave their homes to seek medical assistance. The UI module 460 may receive an input from the user indicating the user's agreement to follow the health regulations, e.g., a verbal agreement received via the microphone 270 that the user will only seek medical assistance while out. The UI module 460 may display additional information or reminders to the user on the interior screen 340 during the ride, such as information about how to obtain health care, information about proper PPE use, information about safe handwashing procedures, etc. In some embodiments, some or all of the information and prompts described above are provided via a user interface of the user's user device 130, and the UI module 460 is executed on the user device 130.

The user access engine 470 selectively enables users to access one or more compartments of the AV 110, such as the passenger compartment 300 or delivery compartments. The user access engine 470 receives signals from the health protocol engine 450 indicating whether the health protocol engine 450 has determined that the user should be permitted to access the AV 110. The user access engine 470 may control locks associated with the doors to one or more compartments to the AV 110, such as a lock on the door handle 290 shown in FIG. 2. In some embodiments, one or more doors of the AV 110 may have automated opening mechanisms, and the user access engine 470 instructs an automated opening mechanism to open the door automatically. Minimizing physical contact points between users and the AV 110, including users touching door handles, can reduce the spread of disease between users.

Example Fleet Management System

Figure 5:
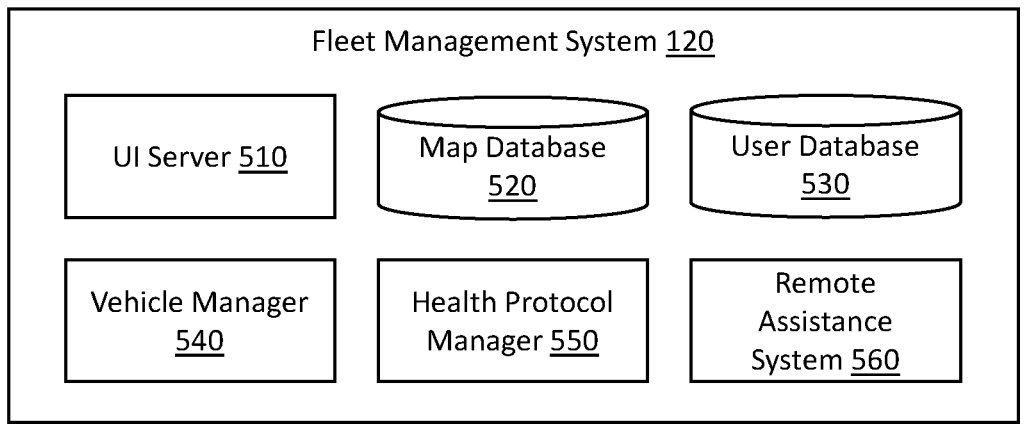
FIG. 5 is a block diagram illustrating a fleet management system according to some embodiments of the present disclosure.

FIG. 5 is a block diagram illustrating the fleet management system 120 according to some embodiments of the present disclosure. The fleet management system 120 includes a UI (user interface) server 510, a map database 520, a user database 530, a vehicle manager 540, a health protocol manager 550, and a remote assistance system 560. In alternative configurations, different, additional, or fewer components may be included in the fleet management system 120. Further, functionality attributed to one component of the fleet management system 120 may be accomplished by a different component included in the fleet management system 120 or a different system than those illustrated.

The UI server 510 is configured to communicate with client devices that provide a user interface to users. For example, the UI server 510 may be a web server that provides a browser-based application to client devices, or the UI server 510 may be a mobile app server that interfaces with a mobile app installed on client devices, such as the user device 130. The user interface enables the user to access a service of the fleet management system 120, e.g., to request a ride from an AV 110, or to request a delivery from an AV 110. For example, the UI server 510 receives a request for a ride that includes an origin location (e.g., the user's current location) and a destination location, or a request for a delivery that includes a pickup location (e.g., a local restaurant) and a destination location (e.g., the user's home address). The user interface provided by or enabled by the UI server 510 may further provide information to the user about the health protocol, request and receive an agreement from the user regarding the health protocol, or conduct other user interactions under the health protocol as described with respect to FIG. 4.

The map database 520 stores a detailed map describing roads and other areas (e.g., parking lots, AV service facilities) traversed by the fleet of AVs 110. The map database 520 includes data describing roadways (e.g., locations of roadways, connections between roadways, roadway names, speed limits, traffic flow regulations, toll information, etc.), data describing buildings (e.g., locations of buildings, building geometry, building types), and data describing other objects (e.g., location, geometry, object type), and data describing other features, such as bike lanes, sidewalks, crosswalks, traffic lights, parking lots, etc. At least a portion of the data stored in the map database 520 is provided to the AVs 110 as a map database 410, described above.

The user database 530 stores data describing users of the fleet of AVs 110. Users may create accounts with the fleet management system 120, which stores user information associated with the user accounts in the user database 530. The user information may include identifying information (name, user name), password, payment information, home address, contact information (e.g., email and telephone number), and information for verifying the user (e.g., photograph, driver's license number). Users may provide some or all of the user information to the fleet management system 120. In some embodiments, the fleet management system 120 may infer some user information from usage data or obtain user information from other sources, such as public databases or licensed data sources. The user database 530 may also store data describing users' use of one or more services provided by the fleet of AVs 110. For example, the user database stores data describing previous rides taken by each user, including origin and destination locations, time, date, data identifying the AV that provided the ride, and data identifying other users in the vehicle for each ride. In other embodiments, the ride data is stored in a separate database that aggregates ride information, including data identifying the AV that provided each ride and users present in the AV during each ride.

The fleet management system 120 may learn one or more home addresses for a user based on various data sources and user interactions. The user may provide a home address when setting up his account, e.g., the user may input a home address, or the user may provide an address in conjunction with credit card information. In some cases, the user may have more than one home, or the user may not provide a home address, or the user-provided home address may not be correct (e.g., if the user moves and the home address is out of date, or if the user's address associated with the credit card information is not the user's home address). In such cases, the fleet management system 120 may obtain a home address from one or more alternate sources. In one example, the fleet management system 120 obtains an address associated with an official record related to a user, such as a record from a state licensing agency (e.g., an address on the user's drivers license), an address from the postal service, an address associated with a phone record, or other publicly available or licensed records. In another example, the fleet management system 120 infers a home address based on the user's use of a service provided by the fleet management system 120. For example, the fleet management system 120 identifies an address associated with at least a threshold number of previous rides provided to a user (e.g., at least 10 rides, at least 50% of rides, or a plurality of rides), or at least a threshold number of previous deliveries (e.g., at least five deliveries, at least 60% of deliveries) as a home address or candidate home address. The fleet management system 120 may look up a candidate home address in the map database 520 to determine if the candidate home address is associated with a residential building type, e.g., a single-family home, a condominium, or an apartment. The fleet management system 120 stores the identified home address in the user database 530. The fleet management system 120 may obtain or identify multiple addresses for a user and associate each address with the user in the user database 530. In some embodiments, the fleet management system 120 identifies a current home address from multiple candidate home addresses, e.g., the most recent address, or an address that the user rides to or from most frequently, and flags the identified current home address in the user database 530.

The vehicle manager 540 directs the movements of the AVs 110 in the fleet. The vehicle manager 540 receives service requests from users from the UI server 510, and the vehicle manager 540 assigns service requests to individual AVs 110. For example, in response to a user request for transportation from an origin location to a destination location, the vehicle manager 540 selects an AV and instructs the AV to drive to the origin location (e.g., a passenger or delivery pickup location), and then instructs the AV to drive to the destination location (e.g., the passenger or delivery destination location). In addition, the vehicle manager 540 may instruct AVs 110 to drive to other locations while not servicing a user, e.g., to improve geographic distribution of the fleet, to anticipate demand at particular locations, to drive to a charging station for charging, etc. The vehicle manager 540 also instructs AVs 110 to return to AV facilities for recharging, maintenance, or storage.

The health protocol manager 550 instructs the health protocol engine 450 of the AV 110 to implement a health protocol. For example, the health protocol manager 550 instructs the AV 110 (e.g., the health protocol engine 450) to determine a body temperature of the user (e.g., a passenger or delivery user) at the origin location prior to enabling the user to access the AV 110. The health protocol manager 550 also instructs the AV 110 to perform disinfecting procedures, such as when to use an on-board disinfecting system, and when to return to an AV facility for disinfecting. For example, the health protocol manager 550 instructs the AV 110 to return to an AV facility for cleaning after the AV 110 has come into contact with a person with an elevated body temperature. More particularly, after the AV 110 has maneuvered a symptomatic passenger to the destination location and the passenger has exited the AV 110, the health protocol manager 550 instructs the AV 110 to maneuver to a cleaning facility for disinfecting the interior and exterior of the AV 110. The health protocol manager 550, or the vehicle manager 540, may select an AV facility from a set of AV facilities based on the location of the AV 110 and the locations of the AV facilities, the staffing levels of the AV facilities, the number of other AVs queued for cleaning at the AV facilities, or other factors. The health protocol manager 550 may include or interface with the vehicle manager 540 or a separate navigation system that selects a route for an AV 110 to follow based on data in the map database 520.

The health protocol manager 550 may adjust a ride service provided to users based on movement restriction regulations or recommendations. For example, the health protocol manager 550 may implement a rule that the UI server 510 does not allow users to request shared rides with other unrelated passengers. As another example, the health protocol manager 550 may implement a rule not allowing users to request a ride to a location outside a given area, e.g., more than 1 mile from their homes, or more than 1 mile from their homes unless they are traveling to a healthcare facility.

In some embodiments, the health protocol manager 550 performs some or all of the functions described with respect to the health protocol engine 450. In such embodiments, the AV 110 provides data collected by the sensor suite 140, such as a temperature reading, to the fleet management system 120. For example, in the ride context, the health protocol manager 550 then determines if the destination location provided in the request is a permitted destination for a high temperature passenger, and in response to determining that the destination is a permitted destination, instructs the AV 110 to enable the user to enter a passenger compartment of the AV 110.

The health protocol manager 550 may gather data that can be used for contact tracing of symptomatic users. The fleet management system 120 stores detailed information about the use of each AV, including movements of each AV, each user that enters each AV (e.g., user identifier, time and place of the user's entry, time and place of the user's exit, where the user sat in the AV), and when each AV was disinfected. This information may be stored in the user database 530, a ride database, and AV database, or one or more other databases or combination of databases. The health protocol manager 550 may provide a subset of this information to health authorities, such as the national Center for Disease Control (CDC) or state or local health departments, to assist in contact tracing. The fleet management system 120 follows any applicable privacy laws and practices in sharing user data, and may request user consent before sharing certain information with health authorities.

For example, in response to the health protocol manager 550 identifying a symptomatic user, the health protocol manager 550 retrieves data describing other users who came into contact with the symptomatic user within AVs of the fleet 110 over a period of time, e.g., the past week or two weeks. The period of time may be set based on observed durations of infections caused by a particular pathogen. In particular, the health protocol manager 550 identifies any previous rides taken by the user during the time period in the user database 530 or another database. For each of the identified rides, the health protocol manager 550 identifies any other users within the AV while the symptomatic user was in the AV; these users may have been exposed to the pathogen if the symptomatic user was already carrying the pathogen during the shared ride. In addition, the health protocol manager 550 may identify other rides provided by the same AV for a period of time after the symptomatic user exited the AV, e.g., a duration for which the pathogen can survive in the air or on surfaces (e.g., one hour, or one day). In some embodiments, the health protocol manager 550 determines when the AV was next disinfected after the user exited the AV, and gathers all users of the AV during the period of time from when the symptomatic user exited the AV until the AV was disinfected, or until the duration for which the pathogen can survive in the AV has passed. The health protocol manager 550 may perform a similar procedure for contact tracing of users of a delivery fleet, identifying all users who accessed an AV after a symptomatic user and before the AV was disinfected or the duration for which the pathogen can survive on the AV has passed.

The remote assistance system 560 is a system for that allows a human remote assistant to perform manual remote observation of the AV 110 and provide inputs to the AV 110. The fleet management system 120 provides the remote assistance system 560 to enable the remote assistant to observe the AV 110 and provide input when the AV 110 encounters an unusual environment or situation and to assist the AV 110 as needed. The remote assistance system 560 provides user interfaces to the remote assistant displaying, for example, images collected by the sensor suite 140, temperature data collected by the sensor suite 140, and a map showing the location of the AV 110. For example, the remote assistant can view data collected by the AV 110 to determine if a user may be sick, and provide a manual input to the AV 110 based on their determination.

In some embodiments, the remote assistance system 560 enables the remote assistant to communicate in real-time with a user of the AV 110, e.g., through the user device 130, or through output system of the AV 110. For example, the remote assistant can answer user questions or provide additional information about the health protocol. The remote assistant may be able to override decisions made by the health protocol engine 450 or health protocol manager 550 denying entry to a passenger or other user. For example, if the health protocol engine 450 or health protocol manager 550 cannot verify a companion with a user and therefore prohibits the user and companion from entering the AV 110, the user or companion may provide verifying information to the remote assistant, who many provide a user input overriding the prior decision. In response to the user input, the remote assistance system 560 transmits an instruction to the AV 110 enabling the user to access the AV 110.

Example Method for Applying a Health Protocol for a Ride Service

Figure 6:
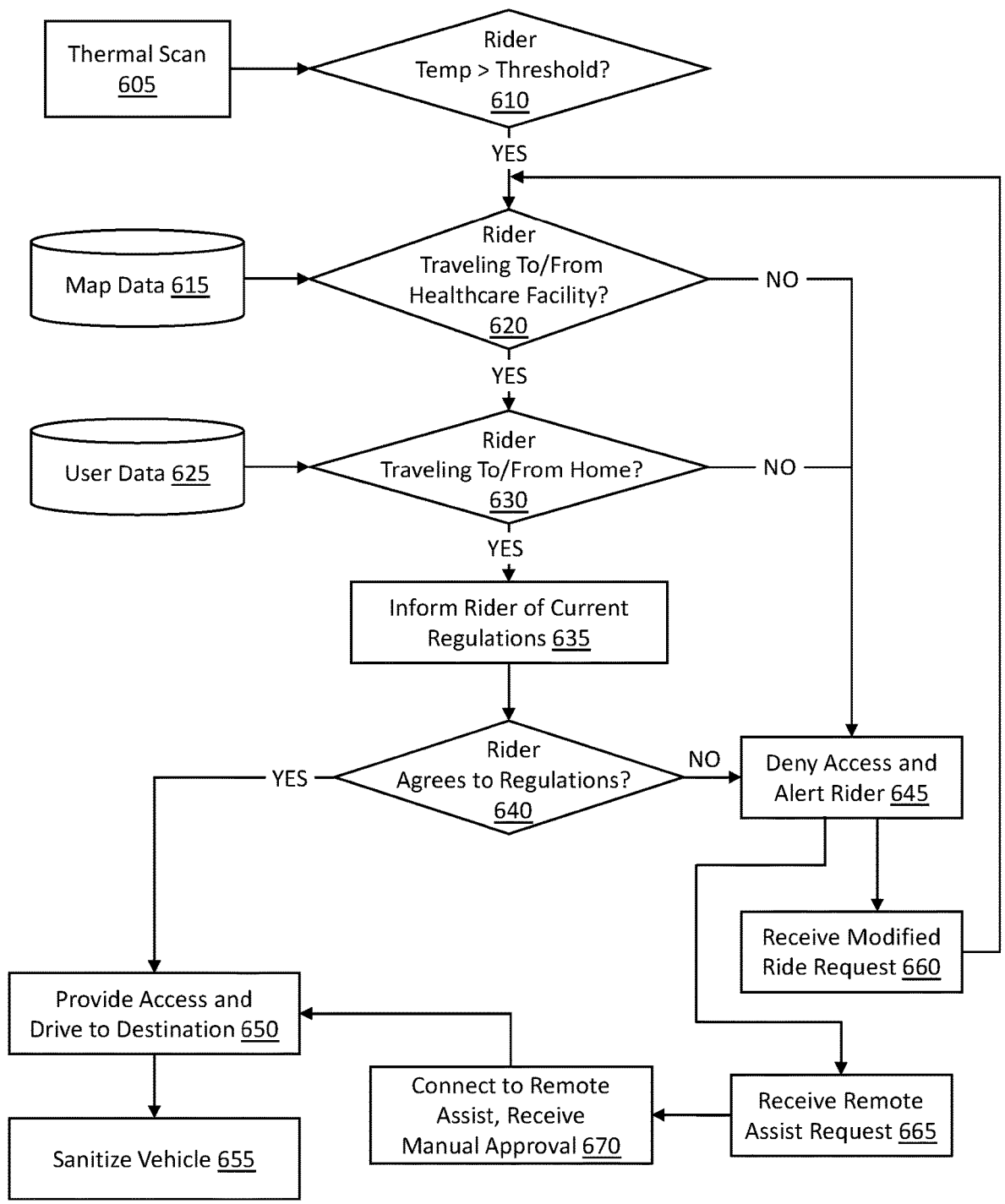
FIG. 6 illustrates a flow diagram showing a process applying a health protocol in an AV ride service according to some embodiments of the present disclosure.

FIG. 6 illustrates a flow diagram showing a process applying a health protocol in an AV ridesharing service according to some embodiments of the present disclosure. The AV 110 obtains a thermal scan 605 of a rider, e.g., the user 220, using a thermal sensor, such as the thermal sensor 230 or 320. The AV 110 (e.g., the health protocol engine 450) compares 610 the rider temperature indicated by the thermal scan 605 to a threshold, e.g., 100° F. If the temperature does not exceed the threshold, the AV 110 may proceed with the ride as normal (not shown in FIG. 6). If the temperature exceeds the threshold, the AV 110 (e.g., the health protocol engine 450) determines 620 if the rider is traveling to or from a healthcare facility based on map data 615. The map data 615 may include data in the map database 410 or map database 520, and may indicate the building type (e.g., if the building is a hospital, medical office, or pharmacy). If the rider is traveling to or from a healthcare facility, the AV 110 (e.g., the health protocol engine 450) determines 630 if the rider is traveling to or from the rider's home based on user data 625. The user data 625 may be data from the user database 530 that is transmitted from the fleet management system 120 to the AV 110, or the fleet management system 120 (e.g., the health protocol manager 550) may perform the determination 630. If the rider is traveling to or from home (i.e., the rider is traveling from a healthcare facility back home, or from home to a healthcare facility), the AV 110 informs 635 the rider of current regulations regarding the movement of people, e.g., that the rider may only travel to seek medical advice, that the rider should wear a mask in public, that the rider should avoid coming into contact with other people other than for seeking medical advice, etc. If the rider agrees 640 to the regulations, the AV 110 provides 650 access to the passenger compartment and drives the rider to the rider's requested destination. After the AV 110 drops off the rider, the AV 110 sanitizes 655 the vehicle using an on-board disinfecting system and/or driving to a facility for cleaning.

If the rider is not traveling to or from a healthcare facility (decision 620), is not traveling to or from the rider's home address (decision 630), or does not agree to the regulations (decision 640), the AV 110 denies 645 the rider access to the AV 110 and alerts the rider using a user interface of the AV 110 or user device 130. After the rider has been denied access, the rider may input a modified ride request, e.g., a request to a different destination. The AV 110 or fleet management system 120 (e.g., the UI server 510) receives 660 the modified ride request, and the process continues at decision 620 to review the modified ride request. Alternatively, the rider may request to connect to a remote assistant via the remote assistance system 560. The AV 110 or fleet management system 120 receives 665 the remote assist request and connects 670 the rider to a remote assistant. The remote assistant may provide information about the current regulations, manually input a modified ride, override one of the prior decision 620, 630, or 640 (e.g., if the rider verbally agrees to the regulations to the remote assistant, or provides proof of a home address to the manual assistant), or perform other actions. If the remote assistant provides manual approval of the ride, with or without modifications, the AV 110 provides access to the AV 110 and drives the rider to the destination.

Example Method for Identifying a Location for a Target Object

Figure 7:
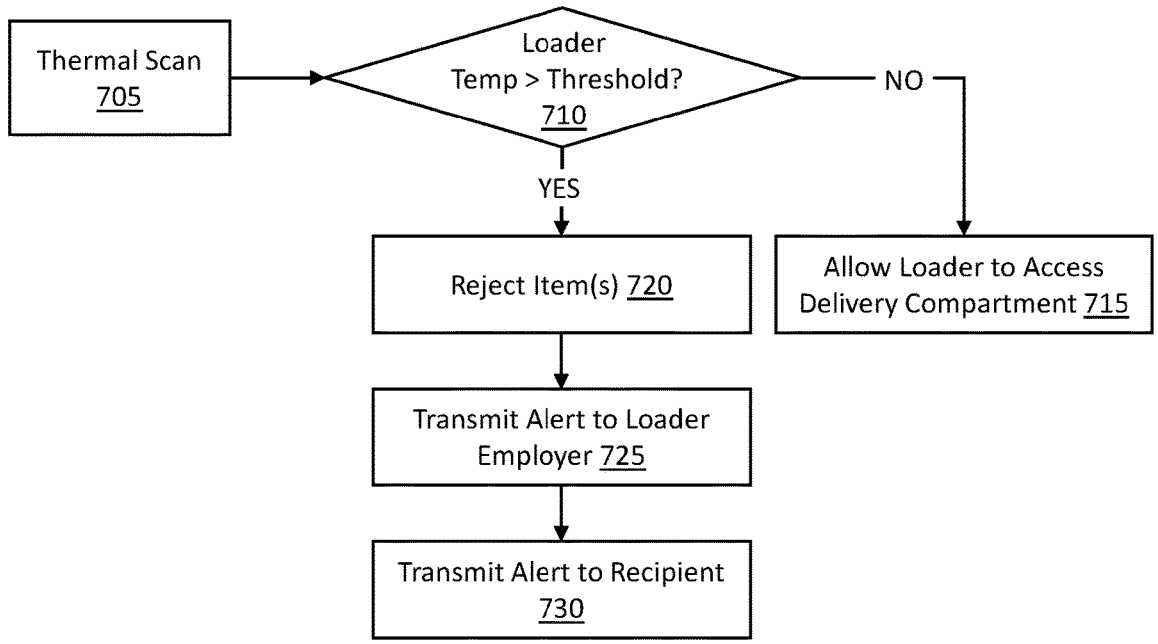
FIG. 7 illustrates a flow diagram showing a process for applying a health protocol when accepting an item for delivery by an AV according to some embodiments of the present disclosure.

FIG. 7 illustrates a flow diagram showing a process for applying a health protocol when accepting an item for delivery by an AV according to some embodiments of the present disclosure. The AV 110 obtains a thermal scan 705 of a loader (i.e., a person attempting to a load an item for delivery into the AV 110) using a thermal sensor, such as the thermal sensor 230 or 320. The AV 110 (e.g., the health protocol engine 450) compares 710 the loader temperature indicated by the thermal scan 705 to a threshold, e.g., 100° F. If the temperature does not exceed the threshold, the AV 110 allows 715 the loader to access a delivery compartment, e.g., by automatically opening a door or unlocking a door.

If the temperature exceeds the threshold, the AV 110 rejects 720 the items, not allowing the loader to access a delivery compartment. The AV 110 may alert the loader that the loader may not access the AV 110. In addition, the AV 110 or fleet management system 120 may transmit 725 an alert to the loader's employer that the loader is running a fever. This allows the employer to send the loader home or to receive medical treatment, and to take proper precautions with respect to areas or items that the loader may have come into contact with. Lastly, the AV 110 or fleet management system 120 transmits 730 an alert to the recipient that the item could not be delivered. In some embodiments, the fleet management system 120 or loader's employer may make alternate arrangements to get the item to the recipient, e.g., sourcing the item from another location.

Figure 8:
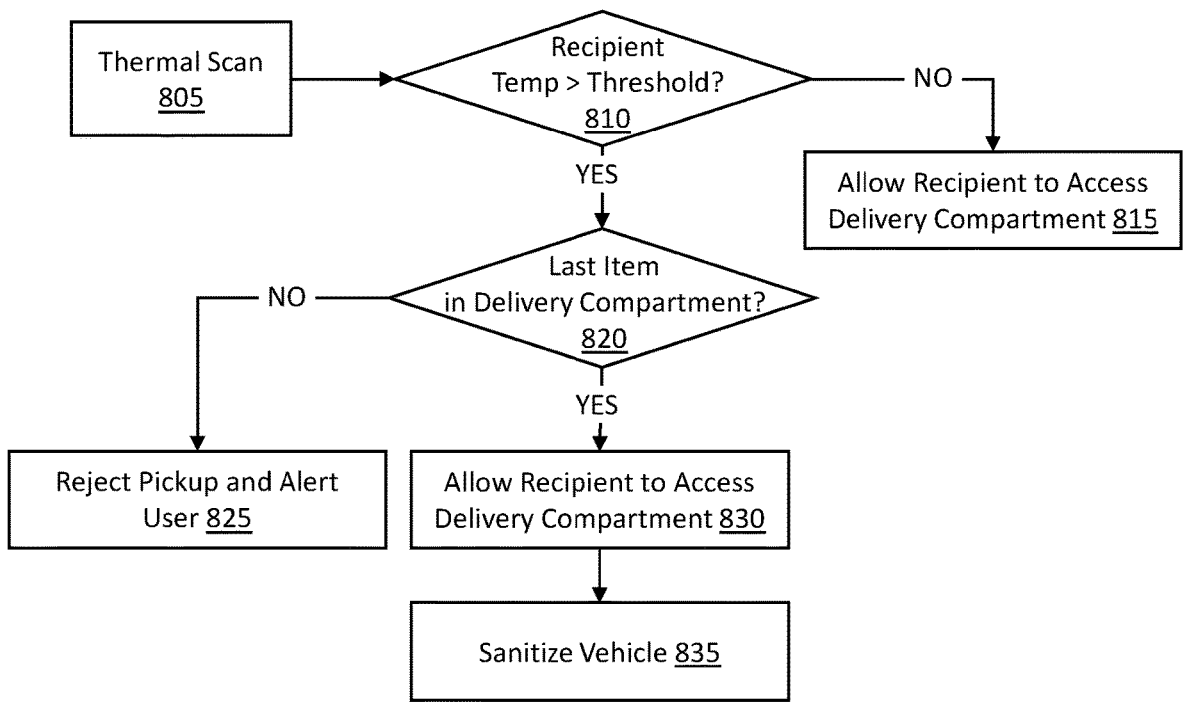
FIG. 8 illustrates a flow diagram showing a process for applying a health protocol when delivering an item by an AV according to some embodiments of the present disclosure.

FIG. 8 illustrates a flow diagram showing a process for applying a health protocol when delivering an item by an AV according to some embodiments of the present disclosure. The AV 110 obtains a thermal scan 805 of a recipient (i.e., a person attempting to a retrieve an item for delivery from the AV 110) using a thermal sensor, such as the thermal sensor 230 or 320. The AV 110 (e.g., the health protocol engine 450) compares 810 the recipient temperature indicated by the thermal scan 805 to a threshold, e.g., 100° F. If the temperature does not exceed the threshold, the AV 110 allows 815 the recipient to access a delivery compartment, e.g., by automatically opening a door or unlocking a door.

If the temperature exceeds the threshold, the AV 110 determines 820 whether the item is the last item in the delivery compartment. If not, and other items are in the delivery compartment for delivery to other recipients, the AV 110 rejects 825 the pickup and alerts the recipient. In some embodiments, the AV 110 may make other deliveries to other recipients, and after the other deliveries have been made, returns to the symptomatic recipient and allows the recipient to access the delivery compartment. If the item is the last item in the delivery compartment, the AV 110 allows 830 the recipient to access the delivery compartment and collect the item(s) for delivery. After the recipient has accessed the delivery compartment, the AV 110 disinfects 835 the vehicle, or the portion of the vehicle that the recipient came into contact with, before continuing service.

Select Examples

Example 1 provides a method for operating a ride service that includes detecting, with a thermal sensor mounted on an autonomous vehicle (AV), a body temperature of a user of the AV; comparing the detected body temperature to a threshold temperature; and, in response to determining that the detected body temperature of the user exceeds the threshold temperature, retrieving a destination of the user, determining if the destination of the user is a permitted destination for a high temperature passenger, and in response to determining that the destination is a permitted destination, enabling the user to enter a passenger compartment of the AV.

Example 2 provides the method according to example 1, where determining if the destination of the user is a permitted destination includes retrieving, from a map database, a building type associated with the destination of the user, and determining that building type is associated with a healthcare service.

Example 3 provides the method according to example 1, where determining if the destination of the user is a permitted destination includes retrieving a home address for the user, wherein the home address is at least one of a home address provided by the user, an address associated with payment information of the user, an address associated with an official record of the user, and an address associated with at least a threshold number of previous rides provided to the user; and determining if the destination of the user matches the retrieved home address for the user.

Example 4 provides the method according to any of examples 1 through 3, further including determining if a pickup location of the user is a permitted pickup location for a high temperature passenger, wherein permitted pickup locations include a home address of the user and buildings associated with healthcare services, and enabling the user to enter a passenger compartment of the AV is further in response to determining that the pickup location is a permitted pickup location.

Example 5 provides the method according to any of examples 1 through 4, further including notifying the user that the detected body temperature exceeds the threshold temperature, alerting the user to at least one regulation governing movement of people with body temperatures above the threshold temperature, and receiving, from the user, an input indicating that the user agrees to follow the at least one regulation.

Example 6 provides the method according to any of examples 1 through 5, where enabling the user to enter the AV comprises unlocking a door to a passenger compartment of the AV.

Example 7 provides the method according to any of examples 1 through 6, further including maneuvering the AV to the destination of the user, and, in response to the user exiting the AV at the destination, applying a disinfectant to at least a portion of a passenger compartment of the AV.

Example 8 provides the method according to any of examples 1 through 7, further including maneuvering the AV to the destination of the user, and, in response to the user exiting the AV at the destination, maneuvering the AV to a cleaning facility for disinfecting an interior of the AV and an exterior of the AV.

Example 9 provides the method according to any of examples 1 through 8, further including retrieving an initial destination of the user, the initial destination different from the destination; and in response to determining that the initial destination of the user is not a permitted for a high temperature passenger, determining an alternate destination for the user, where wherein retrieving a destination of a user comprises receiving a modified ride request from the user, the modified request comprising the determined alternate destination.

Example 10 provides the method according to any of examples 1 through 9, further including detecting a second passenger in an environment of the AV based on data captured by at least one of a camera and a lidar sensor, verifying the second passenger as a permitted companion for the user based on an identify of the second passenger and a relationship between the user and the second passenger, and, in response to verifying the second passenger as a permitted companion, enabling the second passenger to enter a passenger compartment of the AV.

Example 11 provides an autonomous vehicle (AV) that includes a thermal sensor, a thermal image processor, a health protocol engine, and a user access engine. The thermal sensor is mounted on an exterior of the AV and is configured to capture a thermal image of a portion of an environment of the AV. The thermal image processor is configured to determine, based on the thermal image, a body temperature of a user of the AV. The health protocol engine is configured to compare the body temperature to a threshold temperature and, in response to determining that the body temperature exceeds the threshold temperature, determine that a destination of the user is a permitted destination for a high temperature passenger. The user access engine is configured to enable the user to enter a passenger compartment of the AV in response to a signal from the health protocol engine indicating that the user is permitted to enter the AV.

Example 12 provides the AV according to example 11, the AV further including a user interface module configured to alert the user to at least one regulation governing movement of people with body temperatures above the threshold temperature, and receive, from the user, an input indicating that the user agrees to follow to the at least one regulation.

Example 13 provides the AV according to example 11 or 12, the AV further including a second thermal sensor mounted in a passenger compartment of the AV, the second thermal sensor configured to capture a second thermal image comprising at least a portion of a user inside the passenger compartment, where the thermal image processor is further configured to determine, based on the second captured thermal image, a body temperature of the user inside the passenger compartment Example 14 provides the AV according to any of examples 11 through 13, where determining that a destination of the user is a permitted destination for a high temperature passenger includes transmitting, to a remote system, a signal indicating that the user has an elevated body temperature, and receiving, from the remote system, a signal indicating that the destination of the user is a permitted destination for a high temperature passenger.

Example 15 provides the AV according to any of examples 11 through 14, the AV further including a disinfecting system configured to distribute a disinfecting material to at least a portion of a passenger compartment of the AV after the user has exited the AV.

Example 16 provides the AV according to any of the examples 11 through 15, the AV further including a camera configured to capture an image of a second portion of the environment of the AV, where the health protocol engine includes an image processor configured to process the captured image to determine if the user is wearing personal protective equipment.

Example 17 provides a system for managing a fleet of autonomous vehicles (AVs) including a user interface server, a vehicle manager, and a health protocol manager. The user interface server is configured to receive a request for a ride from a user, the request comprising an origin location and a destination location. The vehicle manager is configured to instruct a selected AV of the fleet to drive to the origin location. The health protocol manager is configured to instruct the selected AV to determine a body temperature of the user at the origin location prior to enabling the user to access the AV, and, in response to receiving a signal from the selected AV indicating that the body temperature of the user exceeds a threshold temperature, instruct the selected AV to drive to an AV facility for cleaning after the AV reaches the destination location.

Example 18 provides the system according to claim 17, where the health protocol manager is further configured to determine if the destination location provided in the request is a permitted destination for a high temperature passenger, and, in response to determining that the destination is a permitted destination, instructing the AV to enable the user to enter a passenger compartment of the AV.

Example 19 provides the system according to claim 17 or 18, the system further including a remote assistance system configured to receive temperature data and images captured by the AV, provide a real-time communication channel between the user and a remote assistant, and display a user interface to the remote assistant, the user interface configured to display data captured by at least one sensor of the selected AV.

Example 20 provides the system according to claim 19, where the user interface enables the remote assistant to provide a user input overriding a decision by one of the health protocol manager and the AV prohibiting the user from entering a passenger compartment of the vehicle, and the remote assistance system transmits an instruction to the AV to enable the user to enter the passenger compartment of the vehicle.

Example 21 provides an autonomous vehicle (AV) including a thermal sensor, a thermal image processor, a health protocol engine, and a user access engine. The thermal sensor is mounted on an exterior of the AV and is configured to capture a thermal image of a portion of an environment of the AV. The thermal image processor is configured to determine, based on the thermal image, a body temperature of a user of the AV. The health protocol engine is configured to compare the body temperature to a threshold temperature and, in response to determining that the body temperature exceeds the threshold temperature, determine that the user is not presently permitted to access the vehicle. The user access engine is configured to selectively enable the user to access at least one compartment of the AV in response to a signal from the health protocol engine indicating that the user is permitted to access the AV.

Example 22 provides a method for operating a delivery service that includes detecting, with a thermal sensor mounted on an exterior of an autonomous vehicle (AV), a body temperature of a user of the AV, the user having an item for loading into the AV; comparing the detected body temperature to a threshold temperature; and, in response to determining that the detected body temperature of the user exceeds the threshold temperature, preventing the user from loading the item into the AV, and alerting a recipient of the item that the user was prevented from loading the item into the AV.

Example 23 provides a method for operating a delivery service that includes detecting, with a thermal sensor mounted on an exterior of an autonomous vehicle (AV), a body temperature of a user of the AV, where the user is a recipient of an item loaded in a compartment of the AV; comparing the detected body temperature to a threshold temperature; and, in response to determining that the detected body temperature of the user exceeds the threshold temperature, enabling the user to access the compartment of the AV in which the item is loaded, and disinfecting at least a portion of the AV with which the user contacts while accessing of the compartment.

Other Implementation Notes, Variations, and Applications

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

In one example embodiment, any number of electrical circuits of the figures may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

It is also imperative to note that all of the specifications, dimensions, and relationships outlined herein (e.g., the number of processors, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular arrangements of components. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more components. However, this has been done for purposes of clarity and example only. It should be appreciated that the system can be consolidated in any suitable manner. Along similar design alternatives, any of the illustrated components, modules, and elements of the FIGS. may be combined in various possible configurations, all of which are clearly within the broad scope of this Specification.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. Note that all optional features of the systems and methods described above may also be implemented with respect to the methods or systems described herein and specifics in the examples may be used anywhere in one or more embodiments.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph (f) of 35 U.S.C. Section 112 as it exists on the date of the filing hereof unless the words "means for" or "step for" are specifically used in the particular claims; and (b) does not intend, by any statement in the Specification, to limit this disclosure in any way that is not otherwise reflected in the appended claims.

What is claimed is:

1. A method for operating a ride service comprising:
   detecting, with a thermal sensor mounted on an autonomous vehicle (AV), a body temperature of a user of the AV;
   comparing the detected body temperature to a threshold temperature; and
   in response to determining that the detected body temperature of the user exceeds the threshold temperature:
      retrieving a destination of the user,
      determining if the destination of the user is a permitted destination for a high temperature passenger, and
      in response to determining that the destination is a permitted destination, enabling the user to enter a passenger compartment of the AV.

2. The method of claim 1, wherein determining if the destination of the user is a permitted destination comprises:
   retrieving, from a map database, a building type associated with the destination of the user; and
   determining that building type is associated with a healthcare service.

3. The method of claim 1, wherein determining if the destination of the user is a permitted destination comprises:
   retrieving a home address for the user, wherein the home address is at least one of: a stated home address provided by the user, an address associated with payment information of the user, an address associated with an official record of the user, and an address associated with at least a threshold number of previous rides provided to the user; and
   determining if the destination of the user matches the retrieved home address for the user.

4. The method of claim 1, further comprising:
   determining if a pickup location of the user is a permitted pickup location for a high temperature passenger, wherein permitted pickup locations comprise a home address of the user and buildings associated with healthcare services;
   wherein enabling the user to enter a passenger compartment of the AV is further in response to determining that the pickup location is a permitted pickup location.

5. The method of claim 1, further comprising:
   notifying the user that the detected body temperature exceeds the threshold temperature;
   alerting the user to at least one regulation governing movement of people with body temperatures above the threshold temperature; and
   receiving, from the user, an input indicating that the user agrees to follow the at least one regulation.

6. The method of claim 1, wherein enabling the user to enter the AV comprises unlocking a door to the passenger compartment of the AV.

7. The method of claim 1, further comprising:
   maneuvering the AV to the destination of the user; and
   in response to the user exiting the AV at the destination, applying a disinfectant to at least a portion of a passenger compartment of the AV.

8. The method of claim 1, further comprising:
   maneuvering the AV to the destination of the user; and
   in response to the user exiting the AV at the destination, maneuvering the AV to a cleaning facility for disinfecting an interior of the AV and an exterior of the AV.

9. The method of claim 1, further comprising:
   retrieving an initial destination of the user, the initial destination different from the destination; and
   in response to determining that the initial destination of the user is not a permitted destination for a high temperature passenger, determining an alternate destination for the user;
   wherein retrieving a destination of the user comprises receiving a modified ride request from the user, the modified request comprising the determined alternate destination.

10. The method of claim 1, further comprising:
    detecting a second passenger in an environment of the AV based on data captured by at least one of a camera and a lidar sensor;
    verifying the second passenger as a permitted companion for the user based on an identity of the second passenger and a relationship between the user and the second passenger; and in response to verifying the second passenger as a permitted companion, enabling the second passenger to enter a passenger compartment of the AV.

11. An autonomous vehicle (AV) comprising:
a thermal sensor mounted on an exterior of the AV, the thermal sensor configured to capture a thermal image of a portion of an environment of the AV;
a thermal image processor configured to determine, based on the thermal image, a body temperature of a user of the AV;
a health protocol engine configured to:
compare the body temperature to a threshold temperature, and
in response to determining that the body temperature exceeds the threshold temperature, determine that a destination of the user is a permitted destination for a high temperature passenger; and
a user access engine configured to enable the user to enter a passenger compartment of the AV in response to a signal from the health protocol engine indicating that the user is permitted to enter the AV.

12. The AV of claim 11, further comprising a user interface module configured to:
alert the user to at least one regulation governing movement of people with body temperatures above the threshold temperature; and
receive, from the user, an input indicating that the user agrees to follow to the at least one regulation.

13. The AV of claim 11, further comprising a second thermal sensor mounted in the passenger compartment of the AV, the second thermal sensor configured to capture a second thermal image comprising at least a portion of the user inside the passenger compartment, wherein the thermal image processor is further configured to determine, based on the second captured thermal image, a body temperature of the user inside the passenger compartment.

14. The AV of claim 11, wherein determining that a destination of the user is a permitted destination for a high temperature passenger comprises:
transmitting, to a remote system, a signal indicating that the user has an elevated body temperature; and
receiving, from the remote system, a signal indicating that the destination of the user is a permitted destination for a high temperature passenger.

15. The AV of claim 11, further comprising a disinfecting system configured to distribute a disinfecting material to at least a portion of the passenger compartment of the AV after the user has exited the AV.

16. The AV of claim 11, further comprising:
a camera configured to capture an image of a second portion of the environment of the AV;
wherein the health protocol engine comprises an image processor configured to process the captured image to determine if the user is wearing personal protective equipment.

17. A system for managing a fleet of autonomous vehicles (AVs) comprising:
a user interface server configured to receive a request for a ride from a user, the request comprising an origin location and a destination location;
a vehicle manager configured to instruct a selected AV of the fleet to drive to the origin location;
a health protocol manager configured to:
instruct the selected AV to determine a body temperature of the user at the origin location prior to enabling the user to access the selected AV; and
in response to receiving a signal from the selected AV indicating that the body temperature of the user exceeds a threshold temperature, instruct the selected AV to drive to an AV facility for cleaning after the selected AV reaches the destination location.

18. The system of claim 17, wherein the health protocol manager is further configured to:
determine if the destination location provided in the request is a permitted destination for a high temperature passenger; and
in response to determining that the destination is a permitted destination, instructing the selected AV to enable the user to enter a passenger compartment of the selected AV.

19. The system of claim 17, further comprising a remote assistance system configured to:
receive temperature data and images captured by the selected AV;
provide a real-time communication channel between the user and a remote assistant; and
display a user interface to the remote assistant, the user interface configured to display data captured by at least one sensor of the selected AV.

20. The system of claim 19, wherein the user interface enables the remote assistant to provide a user input overriding a decision by one of the health protocol manager and the selected AV prohibiting the user from entering a passenger compartment of the vehicle, and the remote assistance system transmits an instruction to the selected AV to enable the user to enter a passenger compartment of the vehicle.

* * * * *